United States Patent [19]

Linares

[11] Patent Number: 6,030,607

[45] Date of Patent: *Feb. 29, 2000

[54] WATER SOLUBLE SUN TANNING SOLUTION

[75] Inventor: Francisco J. Linares, Miami Lakes, Fla.

[73] Assignee: Biocycle Laboratories, Inc., Miami Lakes, Fla.

[ * ] Notice: This patent issued on a continued prosecution application filed under 37 CFR 1.53(d), and is subject to the twenty year patent term provisions of 35 U.S.C. 154(a)(2).

[21] Appl. No.: 08/831,253

[22] Filed: Apr. 8, 1997

[51] Int. Cl.$^7$ ...................................................... A61K 7/42
[52] U.S. Cl. ............................................. 424/59; 424/401
[58] Field of Search ........................................ 424/59, 401

[56] References Cited

U.S. PATENT DOCUMENTS 5,061,480  10/1991  Marchese et al. ......................... 424/59
5,589,177  12/1996  Herb et al. ............................... 424/401
5,656,280   8/1997  Herb et al. ............................... 424/401

*Primary Examiner*—Shelley A. Dodson
*Assistant Examiner*—Michael A. Williamson
*Attorney, Agent, or Firm*—Liniak, Berenato, Longacre & White, LLC

[57] ABSTRACT

A topical solution that looks and performs like an oil, but with the totally non-oil-like characteristic of being completely water soluble. The present invention utilizes materials that have the oil-like look and feel, i.e. polyoxyethylene ethers, but define an end product which is water soluble. Sun screen active ingredients can also be incorporated into this formulation to yield desired SPF values

12 Claims, No Drawings

6,030,607

WATER SOLUBLE SUN TANNING SOLUTION

BACKGROUND OF THE INVENTION a) Field of the Invention

This invention relates to a product that looks and performs like an oil, but with the totally non-oil-like characteristic of being completely water soluble. The present invention utilizes materials that have the oil-like look and feel, but define an end product which is water soluble. Sun screen active ingredients can also be incorporated into this formulation to yield desired SPF values.

b) Description of Related Art

In the art of sun tanning solutions, sun tanning oils are based on conventional formulations comprised of ingredients such as petroleum derived oils, silicones, or vegetable derived oils, along with some oil soluble man-made or naturally occurring skin emollients.

Typical tanning solutions emphasize the need to provide a solution that is substantially water proof and resistant to rubbing off during use. These prior art solutions are typically resistant to water and perspiration. As a result these prior art solution are also difficult to remove or wash off. While one group of people enjoys going to the beach for both tanning and swimming, another group of people enjoy sun-tanning with oils at the beach only and are not interested in going into the water. For the later group of people, a tan solution that does not rinse off in water is not necessary. In fact, this group of people would prefer a tanning solution that was easy to wash off. Therefore, the need exists for a tanning oil that allows the user to tan for as long as he/she wishes, and then simply rinses off very easily, i.e. with water only. In fact, many individuals avoid tanning oils because of the mess that necessarily accompanies oils.

SUMMARY OF THE INVENTION

It is the primary object of the present invention to use industrial/cosmetic raw materials that have the oil-like look, while providing an end product that is water soluble thereby permitting the user to wash off the product without the use of soap.

It is further the object of the present invention to provide a sun tanning solution having an oil-like feel that is easy to wash off, and thus permits that individual to engage in other activities without the need to go home and shower in order to feel clean.

It is also the object of the present invention to provide a sun tanning solution having an oil-like feel without the side effects normally associated with such oils; i.e., oily and stained clothing, sandy, stained and oily automobile and home or apartment, etc.

These and other objectives of the present invention will become apparent with references to the following detailed description.

DETAILED DESCRIPTION OF THE PREFERRED EMBODIMENT

The present invention is a thin, crystal clear oil-like formulation that has all of the characteristics of oil, but unlike traditional oil is completely water soluble. Sun screen active ingredients listed below as Table 1 can also be incorporated into this formulation to yield desired SPF values. The preferred embodiment is based on a family of material ingredients commonly known as polyoxyethylene ethers (see Table 2 below). It should be understood, however, that the present invention is not intended to be limited in any manner by the preferred embodiment but is limited in scope only by the prior art relevant to this invention.

TABLE 1

| FDA Accepted and Approved Sunscreen Active Ingredients | |
| --- | --- |
| Category I Sunscreens | Approved % |
| Oxybenzone | 2.0–6.0 |
| Sulisobenzone | 5.0–10.0 |
| Dioxybenzone | 3.0 |
| Menthyl Anthranilate | 3.5–5.0 |
| Aminobenzioc Acid | 5.0–15.0 |
| Amyl Dimethyl Paba | 1.0–5.0 |
| 2-Ethoxyethyl p-Methoxy Cinnamate | 1.0–3.0 |
| Diethanolamine p-Methoxy Cinnamate | 8.0–10.0 |
| Digalloyl Trioleate | 2.0–5.0 |
| Ethyl 4-bis (Hydroxypropyl) Aminobenzoate | 1.0–5.0 |
| 2-Ethylhexyl-2-cyano-3, 3-Diphenylacrylate | 7.0–10.0 |
| Ethylhexyl p-Methoxy Cinnamate | 2.0–7.5 |
| 2-Ethylhexyl Salicylate | 3.0–5.0 |
| Glyceryl Aminobenzoate | 2.0–3.0 |
| Homomenthyl Salicylate | 4.0–15.0 |
| Lawsone with Dihydroxyacetone | 3.0 |
| Octyl Dimethyl Paba | 1.4–8.0 |
| 2-Phenylbenzimidazole-5-Sulfonic Acid | 1.0–4.0 |
| Triethanolamine Salicylate | 5.0–12.0 |
| Red Petrolatum | 30.0–100.0 |
| Titanium Dioxide | 2.0–25.0 |

TABLE 2

| Polyoxyethelene Ethers: |
| --- |
| PPG-3-BUTETH-5 |
| PPG-5-BUTETH-7 |
| PPG-7-BUTETH-10 |
| PPG-9-BUTETH-12 |
| PPG-12-BUTETH-16 |
| PPG-15-BUTETH-20 |
| PPG-20-BUTETH-30 |
| PPG-28-BUTETH-35 |
| PPG-33-BUTETH-45 |
| and others. |

The oil-like phase is the predominant phase in this formulation and is comprised of polyoxyethylene ethers or like ingredients. This phase will also contain all of the oil soluble ingredients, such as but not limited to, the oil soluble sunscreen active ingredients, the essential oils, the silicone oils, petroleum derived oils, vegetable oils, oil soluble emollients, oil soluble preservatives; in general, any oil soluble ingredient that can be added in a predetermined amount to enhance the performance of the formulation without detracting from the primary objective of provide a solution that is completely water soluble.

The predominant aqueous phase ingredient is water. The amount of water present in the formulation will vary according to the amount of water soluble ingredients incorporated into a particular version or formulation of the invention. These water soluble ingredients may be, but are not limited to, water soluble sunscreen active ingredients, water soluble polymers, water soluble preservatives, water soluble tanning accelerators, water soluble self-tanning ingredients, water soluble emollients; in general, any water soluble ingredient that can be added in a predetermined amount to enhance the performance of the formulation while still maintaining the oil-like characteristics of the final product.

The oil-like phase ingredients are blended together with or without heat until completely dissolved or solubilized. If there are not water soluble ingredients to incorporate into the final product the formulation is finished at this point. (see Example 1 below). Example 1. Percentage Composition By Weight of Water Free Formulation SPF 2 to 4.

| OIL-LIKE PHASE | |
| --- | --- |
| Polyoxyethylene Ethers (see Table 2) | Q.S. to 100.00 |
| Octyl Methoxycinnamate | 2.00 |
| Essential Oil | 0.50 |
| Preservative(s) | (AR) |
| | 100.00 |

If the final product incorporates water soluble ingredients, these ingredients that are not directly soluble in the oil-like phase need to be pre-dissolved, or pre-solubilized in the water phase (hot or cold depending on the ingredient in question), before both phases can be combined. The water phase can be added slowly to the oil-like phase (or vice versa depending on the formulation at hand) with adequate agitation. The final product will be crystal clear non-emulsion with an oil-like appearance, feel and consistency. (see Example 2 below). In Example 2, mixture A is a mixture of hydrolyzed collagen, acetyl tyrosine, and adenosine triphosphate. An example of mixture A is generally known and is being sold under the trademark "Unipertan P-242".

Example 2. Percentage Composition By Weight of a Two Phase Formulation SPF 2 to 4.

| OIL-LIKE PHASE | |
| --- | --- |
| Polyoxyethylene Ethers (see Table 2) | Q.S. to 100.00 |
| Octyl Methoxycinnamate | 2.00 |
| Essential Oil | 0.50 |
| Preservative(s) | (AR) |
| | 100.00 |

| WATER PHASE | |
| --- | --- |
| Deionized Water | 25.00 |
| Mixture A | 5.00 |
| Preservative(s) | (AR) |
| | 100.00 |

It is evident upon producing Example 2 that the resulting product is a non-emulsion. From the foregoing description and examples, it is clear that the present invention presents an oil-like formulation that offers consumers all of the attributes of oils (tanning and others), but with the convenience of being completely water soluble. The present invention finds many applications in the field of hair care and skin care, areas where traditional oils are very popular. Nevertheless, the preferred embodiment of the present invention is a tanning oil; not only outdoor sun tanning, but also indoor salon tanning where existing traditional tanning oils damages the tanning beds.

The present invention offers the consumer the user-friendly characteristic of being rinsable with water in the absence of soap or detergent; thus, a public shower or faucet such as typically found at a beach is sufficient to completely rinse the product off of the skin and/or article of clothing. The present invention is also emollient in nature, again an additional attribute over the current petroleum derived versions of tanning oils currently taught in the prior art that have a tendency to be drying on the skin.

Various optional ingredients may be included in the compositions of the present invention, these include but are not limited to perfumes, preservatives, antiseptics, antibacterials, stabilizers, antioxidants, vitamins, pigments, dyes, as well as other classes of materials whose presence may be cosmetically, medicinally or otherwise desirable.

The present invention may also incorporate skin tanning agents including but not limited to hydroxyaldehydes such as dihydroxyacetone, imidazole, and various imidazole derivatives such s 4-(hydroxymethyllimidazole).

In summary, the present invention offers all of the same attributes that conventional sun-tanning oils offer, yet the present invention surpasses the prior art in natural emolliency, versatility in formulating (ease with which oil soluble and water soluble ingredients are combined), and most important, it allows the users to completely remove the product from their bodies and clothes with ease.

While the forgoing invention has been described in relation to several examples, it will be understood by those of skill in the art that various changes in form and detail may be made without departing from the spirit and scope of the present invention.

I claim:

1. A topical composition comprising a non-emulsion, single solution in a cosmetically effective amount having an appearance, consistency, and feel of oil to a user applying the single solution topically, wherein said single solution is completely water soluble such that the user can completely remove said topical composition with water, wherein said topical composition comprises at least one polyoxyethylene ether and at least one sunscreen active ingredient in amounts and proportions that provide sunscreen protection.

2. The composition of claim 1, wherein said single solution includes an oil substitute.

3. The composition of claim 1, wherein said solution comprises a water phase and a second phase having the characteristics of oil substituted for actual oil.

4. The composition of claim 1, wherein said solution includes a water phase in addition to said at least one polyoxyethylene ether.

5. The composition of claim 5, and further comprising at least one oil-soluble ingredient selected from the group consisting of an essential oil, a silicone oil, a petroleum derived oil, a vegetable oil, an oil-soluble emollient, and an oil-soluble preservative.

6. The composition of claim 4, wherein said water phase comprises at least one water-soluble ingredient selected from the group consisting of a water-soluble polymer, a water-soluble emollient, a water-soluble preservative, a water-soluble tanning accelerator, and a water-soluble self-tanning ingredient.

7. The composition of claim 1, wherein said composition is a clear liquid.

8. The composition of claim 1, further comprising Octyl Methoxycinnamate and an essential oil.

9. The composition of claim 8, further comprising at least one preservative.

10. The composition of claim 8, further having a water phase comprising deionized water and a mixture of hydrolyzed collagen, acetyl tyrosine, and adenosine triphosphate.

11. The composition of claim 1, wherein at least one of said at least one sunscreen active ingredient is water-soluble.

12. The composition of claim 1, wherein at least one of said at least one sunscreen active ingredient is oil-soluble.

* * * * *